(12) United States Patent
Viswanathan

(10) Patent No.: US 8,192,374 B2
(45) Date of Patent: Jun. 5, 2012

(54) ESTIMATION OF CONTACT FORCE BY A MEDICAL DEVICE

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1596 days.

(21) Appl. No.: 11/484,884

(22) Filed: Jul. 11, 2006

(65) Prior Publication Data

US 2007/0021742 A1    Jan. 25, 2007

Related U.S. Application Data

(60) Provisional application No. 60/700,269, filed on Jul. 18, 2005.

(51) Int. Cl.
*A61B 5/103* (2006.01)
*A61B 5/117* (2006.01)
*A61B 5/05* (2006.01)
*A61B 17/00* (2006.01)
*A61B 18/04* (2006.01)

(52) U.S. Cl. ............ 600/587; 600/424; 606/1; 606/27; 606/28; 606/32; 606/34

(58) Field of Classification Search ................. 600/587, 600/593, 594, 595
See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |

(Continued)

*Primary Examiner* — Max Hindenburg
*Assistant Examiner* — Adam Eiseman
(74) *Attorney, Agent, or Firm* — Harness, Dickey & Pierce, P.L.C.

(57) ABSTRACT

A method is provided for establishing contact of a medical device against a tissue surface within a subject body, the method comprising determination of the geometrical configuration of the distal portion of the medical device, and using this together with known control variable information to determine and control the contact force of the distal tip of the medical device against the tissue surface.

24 Claims, 1 Drawing Sheet

U.S. PATENT DOCUMENTS

| | | |
|---|---|---|
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 2001/0038683 A1 | 11/2001 | Ritter et al. |
| 2002/0019644 A1 | 2/2002 | Hastings et al. |
| 2002/0177789 A1 | 11/2002 | Ferry et al. |
| 2004/0006301 A1 | 1/2004 | Sell et al. |
| 2004/0019447 A1 | 1/2004 | Shachar |
| 2004/0064153 A1 | 4/2004 | Creighton, IV et al. |
| 2004/0068173 A1 | 4/2004 | Viswanathan |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2005/0020911 A1 | 1/2005 | Viswanathan et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |

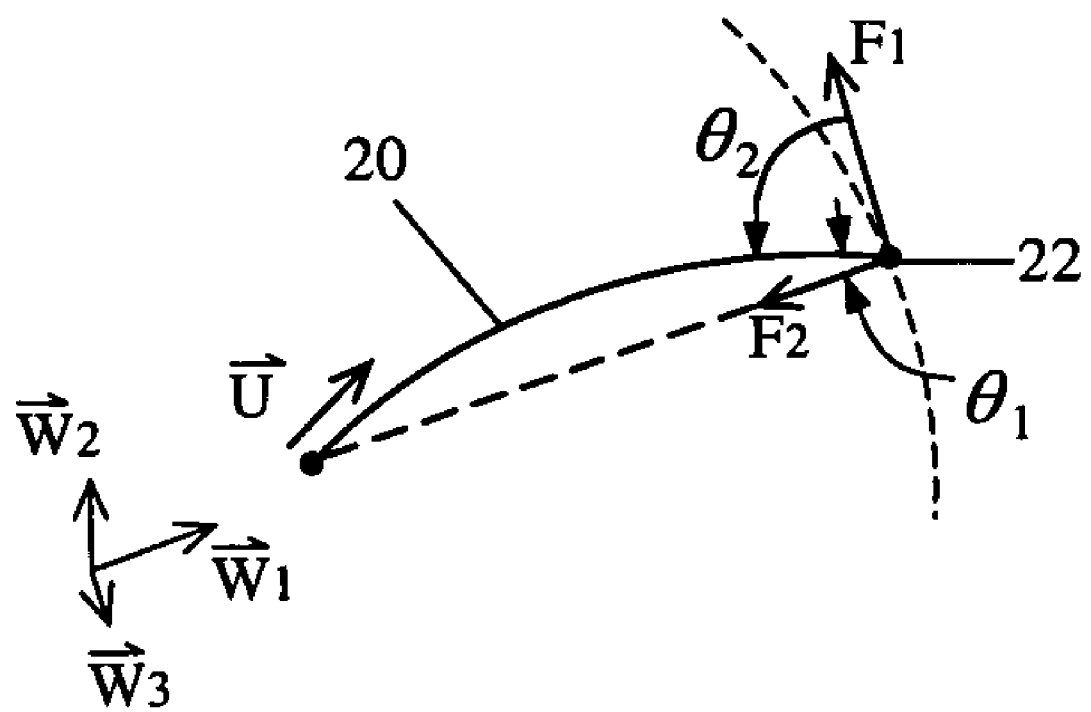

ESTIMATION OF CONTACT FORCE BY A MEDICAL DEVICE

CROSS-REFERENCE TO RELATED APPLICATIONS

This application claims the benefit of U.S. Provisional Patent Application Ser. No. 60/700,269, filed Jul. 18, 2005, the entire disclosure of which is incorporated herein by reference.

FIELD

This invention relates to control of medical devices in a subject body, and more particularly to estimation of contact force of a medical device against a tissue surface within the subject body.

BACKGROUND

Interventional medicine is the collection of medical procedures in which access to the site of treatment is made through one of the patient's blood vessels, body cavities or lumens. For example, electro-physiology mapping of the heart is most often performed using a catheter which may be inserted into a patient's arterial system through a puncture of the femoral artery in the groin area. Other interventional medical procedures include assessment and treatment of tissues on the inner surfaces of the heart (endocardial surfaces) accessed via peripheral veins or arteries, treatment of vascular defects such as cerebral aneurysms, removal of embolic clots and debris from vessels, treatment of tumors via vascular access, endoscopy of the intestinal tract, etc.

Interventional medicine technologies have been applied to manipulation of instruments which contact tissues during surgical procedures, making these procedures more precise, repeatable and less dependent of the device manipulation skills of the physician. Some presently available interventional medical systems for directing and manipulating the distal tip of a medical device by actuation of the distal portion of the device use computer assisted navigation and an imaging system for providing imaging of the device and blood vessels and tissues. Such systems can control the navigation of a medical device, such as a catheter, to a target destination in an operating region using a computer to orient and guide the distal tip through blood vessels and tissue. In some cases, when the computed direction for reaching the target destination is determined and the medical device is extended, it is desired to establish sufficient contact of the medical device with the intended target location on the three dimensional tissue surface. Adequate contact with the tissue surface within the subject body is important, for instance, in the analysis and treatment of cardiac arrhythmias. A method is therefore desired for controlling movement of a medical device that will establish adequate contact with the target tissue surface, estimate such contact force and will allow for treatment of the targeted area.

SUMMARY

The method and apparatus of the present invention facilitates the placement of the distal end of a medical device, such as a catheter or micro-catheter, against a target location on a three-dimensional curved surface within a subject body. Generally, the present invention provides a method for estimating the contact force of a medical device against a surface within a subject body, comprising obtaining three dimensional geometry information for the distal portion of the medical device, constructing a curve representative of the distal portion of the medical device from the pivot point to the tip of the known medical device, estimating the local rotation rate of the flexible portion of the distal portion of the medical device, and, estimating the contact force based on this data and the (known) bending stiffness and the total torque applied to the flexible portion of the medical device.

In one aspect of the present invention, a three-dimensional surface geometry is suitably rendered in an image model and registered with a known location within the subject body. A virtual model may be used in the estimation of the contact force of the medical device against the tissue surface, and in predicting a magnetic field to be applied to the medical device to establish a desired contact force against a target surface within the subject body. From the geometry of the medical device, a net bending moment may be estimated for the distal portion of the medical device. The estimated contact force may then be determined based on the net bending moment and the estimated torque applied to the medical device. The method may further provide the feature of determining an external magnetic field to be applied to the medical device for providing a desired estimated contact force against the tissue surface within the subject body. These and other features and advantages will be in part apparent, and in part pointed out hereinafter.

BRIEF DESCRIPTION OF THE DRAWINGS

FIG. 1 is an illustration of a curved three dimensional tissue surface and a medical device held in contact with the surface through the over-torque method in accordance with the principles of the present invention.

DETAILED DESCRIPTION

In a preferred embodiment of the present invention, a method for establishing and estimating the contact force of the tip of a medical device against a tissue surface within a subject body is provided in accordance with the principles of the present invention. In one embodiment, the method provides for estimating the contact force of a medical device with a tissue surface such as the heart, through the suitable estimation of the torque applied to the medical device via a magnetic field. While this embodiment is operable with magnetically navigable medical devices, other embodiments of a method in accordance with the present invention may be used with medical devices that are guided without magnetic navigation but instead use other control methods for remote navigation such as mechanical actuation, electrostrictive actuation, or hydraulic actuation. The method for estimating the contact force of a medical device against a surface within a subject body comprises obtaining three dimensional geometry information for the distal portion of the medical device, constructing a curve representative of the distal portion of the medical device from the pivot point to the tip of the known medical device, estimating the local rotation rate of the flexible portion of the distal portion of the medical device, determining a net bending moment for the distal portion of the medical device, estimating the contact force based on the (known) bending stiffness, the bending moment and the torque applied to the flexible portion of the medical device, and determining an external magnetic field to be applied to the medical device for providing a desired estimated contact force against the tissue surface within the subject body.

A medical device such as a catheter may be navigated to the interior of a subject body of a patient by various means, including but not limited to magnetic navigation. Once the medical device has been navigated to a target surface of the body, such as a heart wall, the tip of the medical device, the pivot point of the medical device, and at least two intermediate points may be defined in at least two X-ray projections by user-marking to construct (computationally, by interpolation) a three dimensional curve of the medical device as shown in FIG. 1. This curve may be written in the form of $\vec{x}(s)$ where $s \in [0,1]$. Let $s=0$ correspond to the distal end of the medical device, and $s=1$ correspond to the pivot point. The interval $[0,1]$ is then divided computationally into a predetermined number of increments so that $(\vec{x}_1, \ldots \vec{x}_n)$, are a set of points from the distal tip of the medical device to the pivot point. The lengths of each individual segment between the points may be written as $l_i = |\vec{x}_{i+1} - \vec{x}_i|$ until the pivot point is reached. Each segment position that is near a magnet is preferably marked. We can let $\vec{x}_k$ be the approximate location of a magnet on the medical device, and let:

$$\vec{u}_1 = \frac{(\vec{x}_{k-1} - \vec{x}_k)}{|\vec{x}_{k+1} - \vec{x}_k|} \equiv \frac{(\vec{x}_{k-1} - \vec{x}_k)}{l'_1}, \text{ and}$$

$$\vec{u}_2 = \frac{(\vec{x}_k - \vec{x}_{k+1})}{|\vec{x}_k - \vec{x}_{k+1}|} \equiv \frac{(\vec{x}_k - \vec{x}_{k+1})}{l'_2}$$

to define the segments nearest the magnet at $\vec{x}_k$

As an alternative to user-marking of the device on 2 X-ray projections, image processing could be employed to identify the distal portion of the medical device in each projection and thence to determine computationally the three dimensional curve corresponding to the distal portion of the medical device.

Defining the vector $\vec{V}'$ at the magnet location $\vec{x}_k$ as shown below, we can define the unit vector $\vec{V}_k$ that gives the orientation of the magnet at location $\vec{x}_k$ as follows:

$$\vec{V}' = (l_2' \vec{u}_1 + l_1' \vec{u}_2) \tag{1}$$

$$\vec{V}_k = \frac{\vec{V}'}{|\vec{V}'|} \tag{2}$$

Let $m_k$ be the known magnetic moment of the magnet at location $\vec{x}_k$, which may be any of the first, second, or n-th magnet from the distal tip of the given medical device. The torque resulting from the magnet at $\vec{x}_k$ having an orientation $\vec{V}_k$ may be written as the product shown below, where $\vec{B}$ is the applied external magnetic field.

$$\vec{\tau}_k = m_k (\vec{V}_k \times \vec{B}) \tag{3}$$

Let the total magnetic torque acting on the medical device due to all of the magnets be:

$$\vec{\tau}_{magnet} = \Sigma_{magnets} \vec{\tau}_k \tag{4}$$

Let (n+1) index the pivot point (n=50 in the present example). Let:

$$\vec{V}_{n+1} = \frac{(\vec{x}_n - \vec{x}_{n+1})}{|\vec{x}_n - \vec{x}_{n+1}|}, \text{ and} \tag{5}$$

$$\vec{V}_{n-1} = \frac{(\vec{x}_{n-1} - \vec{x}_n)}{|\vec{x}_{n-1} - \vec{x}_n|}, \text{ then let}$$

$$\Delta \theta = \cos^{-1}(\vec{V}_{n+1} \cdot \vec{V}_{n-1}), \text{ and let}$$

$$\Delta l = |\vec{x}_n - \vec{x}_{n+1}| + |\vec{x}_{n-1} - \vec{x}_n| \tag{6}$$

to yield the local estimated rotation rate $\omega_k = \Delta \theta / \Delta l$ If index (n+1) or $\vec{x}_{n+1}$ corresponds to a magnet location of the catheter, use instead a nearest point $\vec{x}_m$ on the medical device such that $\vec{x}_m$ is on a flexible or non-magnet segment. Let EI be the bending stiffness of the flexible segment of the medical device corresponding to $\vec{x}_{n+1}$, or the bending stiffness of the flexible segment nearest to the magnet. Let the vector from $\vec{x}_{n+1}$ to the distal tip of the medical device at $\vec{x}_1$ be $$\vec{r} = (\vec{x}_1, \vec{x}_{n+1}) \text{ and} \tag{7}$$

$$r = |\vec{r}|. \text{ Then} \tag{8}$$

The estimated magnitude of the medical device contact force at the distal tip is given below (assuming no other forces in a direction perpendicular to $\vec{r}$):

$$f = \frac{1}{r}(|\vec{\tau}_{magnet}| - EI\omega) \tag{9}$$

The second term in equation (9) above represents the net bending moment of the distal portion of the device. Referring to FIG. 1, the tissue surface of a three dimensional object in a subject body is represented by curve 20 having an interior surface normal vector $\vec{n}$ at a target point indicated at 22. The local surface geometry of the surface may be obtained from a three-dimensional pre-operative image of the anatomy, or from geometric mapping and anatomical 3D reconstruction that may be performed by reconstructing an interpolated anatomical surface based on endocardial surface locations that have been visited with a catheter device and a localization system that is suitably registered with the computer-controlled navigation system. Since the three-dimensional data of the surface is available, the interior surface normal vector $\vec{n}$ at the target location may be determined from this data. The tip of the actual medical device $\vec{x}_1$, or a virtual medical device where localization data is available, is positioned against the tissue surface 20 near the target location 22. Assuming there is no tangential contact force at the tip, let F be the normal contact force. Defining $r' = -r/|r|$, and $\theta = \cos^{-1}(\vec{r}' \cdot \vec{n})$, then the normal contact force F is:

$$F = f / \sin \theta \tag{10}$$

Where a magnetically navigable medical device is used, an applied external field $\vec{B}$ can also be determined for providing an over-torque of the medical device against the tissue surface at a desired estimated contact force F, within certain physically feasible bounds. This may be accomplished by applying a magnetic moment in a direction that provides the over torque (i.e., leads the orientation of the catheter tip by an angle of approximately 90° as measured about an axis that is normal to the plane defined by the catheter tip orientation and the local surface normal), where a suitable torque $\tau_{magnet}$ can be determined from equations (10) and (9).

The rotation rate of the flexible portion of the medical device resulting from the applied torque may also be determined using a virtual medical device within a computational model. In the case where the device actuation system is magnetic, this estimation of the rotation rate of the distal portion of the medical device may be used to estimate the contact force based on a computed magnetic torque applied to the tip of the medical device, based on the model. A subsequent navigational movement of the medical device may be determined to obtain a desired estimated contact force for improved electro-physiology electrical readings, or to apply improved ablation treatment. A suitable magnetic field for producing a desired force for the medical device can be estimated using the local surface geometry of the target location within the body. Likewise, a virtual representation of the medical device may be suitably rendered in a three-dimensional model of the surface geometry. Such virtual modeling of the medical device may be used to predict the rotation of the medical device prior to movement of the actual medical device. In the above example, we describe the particular case where magnetic field actuation is used to remotely navigate the medical device, as a non-limiting example of an actuation method. Other actuation techniques could be employed as would be familiar to persons skilled in the art of remote surgical navigation, for example a mechanically actuated system where the actuation is based on a system of pull-wires and electronically controlled servo motors. In such a case where this type of mechanical actuation is used, for example equation (9) above would be replaced by a similar equation involving mechanically applied bending torque.

In use, the medical device may be moved in incremental steps towards the target location at an increment of about 1-5 millimeters. The incremental step is made in association with a three-dimensional image model of the surface geometry, which may determine whether the incremental step results in an image threshold crossing. The above distances are suitable for applications of determining the curvature of certain surfaces such as the interior of a heart. It should be noted that the above distances and increments are exemplary in nature, and may be varied for a variety of applications. The magnet system is controlled to apply a magnetic field in a direction that causes the tip or distal portion of the medical device to be rotated to provide the torque for establishing a desired contact force with the tissue surface. Once the tip has established a desired estimated contact against the tissue surface, the lag between the field vector $\vec{B}_0$ and the actual orientation of the tip 24 can provide an indication that the tip of the medical device is in firm contact with the surface at 24. Likewise, where an imaging system is used, the prolapse or buckling in the distal portion of the medical device 24 that can be seen in the acquired images, or the observation that the device tip has not changed position may also indicate that the tip has established the desired contact with the surface 20. The method of estimating the contact force can be used to predict and drive navigation controls. Additionally the estimated contact force could be displayed to inform the user.

The advantages of the above described embodiment and improvements for estimating contact force, enabling over-torque of a medical device and thereby enhancing device-tissue contact against a three dimensional surface within a subject body, when the device is controlled by a remote navigation system, should be readily apparent to one skilled in the art. The actual controls used by the remote navigation system could comprise actuation schemes employing any one or more of magnetic, mechanical, electrostrictive, hydraulic or other actuation means familiar to those skilled in the art. Additional design considerations may be incorporated without departing from the spirit and scope of the invention. Accordingly, it is not intended that the invention be limited by the particular embodiment or form described above, but by the appended claims.

What is claimed is:

1. A method for establishing controlled contact of a medical device against a tissue surface within a subject body by a computer controlled navigation system, the method comprising the computer controlled navigation system:
   receiving an input of discrete data indicative of the geometry of the distal portion of the medical device;
   computationally constructing a curve representative of the distal portion of the medical device from a pivot point to the tip of the medical device;
   estimating from this curve the local rotation rate of the flexible portion of the distal portion of the medical device; and
   estimating the contact force based on the rotation rate, a known bending stiffness and the estimated torque applied to the distal portion of the medical device.

2. The method of claim 1, where additionally local surface geometry information in a neighborhood of the target location is used to estimate the contact force.

3. The method of claim 2, where the estimated contact force is displayed to a user.

4. The method of claim 2 further comprising establishing contact by incrementally moving a minimum distance towards the tissue surface, and applying a control variable suitable for establishing a torque that will provide a predetermined contact force against the tissue surface.

5. The method of claim 2 wherein the surface geometry is derived from a pre-operative image that is suitably registered with the subject body.

6. The method of claim 2 wherein the surface geometry is obtained from an anatomical map derived from a localization system that maps the local surface geometry.

7. The method of claim 6 wherein the medical device is a localized device sending tip position and orientation data to a remote navigation system used for device actuation and control.

8. The method of claim 1, where the estimated contact force is displayed to a user.

9. The method of claim 1, further comprising determining an external magnetic field to be applied to the subject body and distal end of the medical device for providing a desired estimated contact force against the tissue surface within the subject body.

10. The method of claim 9, where the desired estimated contact force against the tissue surface provides for enhanced ablation of the tissue surface.

11. The method of claim 10, where the contact of the distal end of the medical device against the tissue surface is driven by an externally applied magnetic field that applies a magnetic torque to the medical device to provide enhanced contact against the tissue surface.

12. The method of claim 9 wherein the medical device is a magnetically navigable device.

13. The method of claim 1 further comprising establishing contact by incrementally moving a minimum distance towards the tissue surface, and applying a control variable suitable for establishing a torque that will provide a predetermined contact force against the tissue surface.

14. The method of claim 13, where the control variable is an externally applied magnetic field.

15. The method of claim 13, where the control variable is a mechanical control variable.

16. A method for establishing controlled contact of a medical device against a three-dimensional tissue surface within a subject body by a computer controlled navigation system, the method comprising the computer controlled navigation system: obtaining three dimensional geometry information for the distal portion of the medical device, constructing a curve representative of the distal portion of the medical device from the pivot point to the tip of the medical device, estimating the local rotation rate of the flexible portion of the distal portion of the medical device, estimating the current contact force based on the rotation rate, the bending stiffness and the total torque applied to the flexible portion of the medical device, and determining a control variable to be applied to the medical device for providing a desired estimated contact force against the tissue surface within the subject body.

17. The method of claim 16, where the control variable is an externally applied magnetic field.

18. The method of claim 16, where the control variable is a mechanical control variable.

19. The method of claim 16, where the estimated contact force against the tissue surface provides for enhanced ablation of the tissue surface.

20. The method of claim 16 wherein surface geometry information is additionally employed to determine the contact force.

21. The method of claim 20, where the surface geometry information is derived from a pre-operative image that is suitably registered with the subject body.

22. The method of claim 20 wherein the surface geometry information is obtained from an anatomical map derived from a localization system that maps the local surface geometry.

23. The method of claim 20 wherein the medical device is a magnetically navigable device.

24. The method of claim 20 wherein the method further comprises comparing the angular lag between the magnetic field vector and the actual orientation of the tip of the medical device to verify the establishment of a sufficient degree of contact against the tissue surface.

* * * * *